United States Patent [19]

Fields

[11] Patent Number: 4,533,478
[45] Date of Patent: Aug. 6, 1985

[54] 3-SULFOXY-1,2-PROPYLENE GLYCOLS-1-ESTERS OF TRICYCLO (4.2.2.0$^{2,5}$) DEC-9-ENE-3,4,7,8-TETRACARBOXYLIC ACID

[75] Inventor: Ellis K. Fields, River Forest, Ill.

[73] Assignee: Standard Oil Company (Indiana), Chicago, Ill.

[21] Appl. No.: 659,845

[22] Filed: Oct. 11, 1984

Related U.S. Application Data

[62] Division of Ser. No. 485,670, Apr. 18, 1983, Pat. No. 4,506,093.

[51] Int. Cl.$^3$ ............................................. E21B 43/22
[52] U.S. Cl. ................................ 252/8.55 D; 166/275
[58] Field of Search ............... 252/8.55 D, 8.55 R, 252/8.55 B, 8.5 A, 8.5 B, 8.5 C, 8.5 P; 166/274–276; 560/117

[56] References Cited

U.S. PATENT DOCUMENTS

| | | | |
|---|---|---|---|
| 4,160,038 | 8/1979 | Stournas | 252/8.55 D |
| 4,230,183 | 10/1980 | Kalfoglou | 252/8.55 D |
| 4,326,985 | 4/1982 | Blair, Jr. | 252/8.55 D |
| 4,383,930 | 5/1983 | Argabright et al. | 252/8.55 D |
| 4,426,303 | 1/1984 | Nuckels et al. | 252/8.55 D |
| 4,446,079 | 5/1984 | Hoskin | 252/8.55 D |

*Primary Examiner*—Edward A. Miller
*Assistant Examiner*—T. J. Wallen
*Attorney, Agent, or Firm*—William C. Clarke; William T. McClain; William H. Magidson

[57] ABSTRACT

3-Sulfoxy-1,2-propylene glycols-1-esters of tricyclo (4.2.2.0$^{2,5}$) dec-9-ene-3,4,7,8-tetracarboxylic acid are prepared. These compounds are useful as surfactants, biocides and as cosurfactants in enhanced oil recovery.

1 Claim, No Drawings

3-SULFOXY-1,2-PROPYLENE GLYCOLS-1-ESTERS OF TRICYCLO (4.2.2.0$^{2,5}$) DEC-9-ENE-3,4,7,8-TETRACARBOXYLIC ACID

This is a division of application Ser. No. 485,670, filed Apr. 18, 1983, now U.S. Pat. No. 4,506,093.

FIELD OF THE INVENTION

This invention relates to 3-sulfoxy-1,2-propylene glycols-1-esters of tricyclo(4.2.2.0$^{2,5}$)dec-9-ene-3,4,7,8-tetracarboxylic acid. More particularly, this invention relates to 3-sulfoxy-1,2-propylene glycols-1-esters of tricyclo(4.2.2.0$^{2,5}$)dec-9-ene-3,4,7,8-tetracarboxylic acid wherein the said compounds are of the structural formula I:

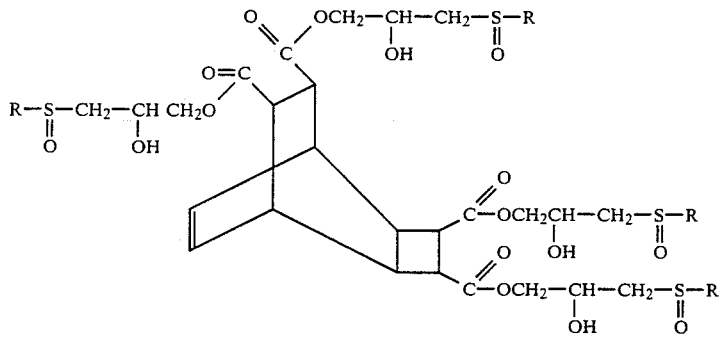

wherein R is selected from the group consisting of aryl radicals derived from benzene, biphenyl, naphthalene, anthracene, and phenanthrene; alkyl moieties of 1 to 22 carbon atoms, and aralkyl moieties, alkylated aryl moieties, and cycloalkyl moieties containing 4 to 40 carbon atoms, the ring radicals of said moieties being selected from the group consisting of phenyl, biphenyl, cyclopentyl, cyclohexyl, phenylnaphthyl, p-tolyl, benzyl, 2-benzothiazyl and 4-pyridyl radicals, wherein R can be substituted with nitro, halogen, cyano and carboalkoxy moieties of 1 to 12 carbon atoms.

For convenience these compounds are referred to as 3-sulfoxy-1,2-propylene glycols-1-esters of tricyclo(4.2.2.0$^{2,5}$)dec-9-ene-3,4,7,8-tetracarboxylic acid. These compounds possess biocidal properties. The invented compounds of molecular weights within the range of from about 400 to about 1200 act as cosurfactants useful in enhanced oil field recovery. These compounds are also useful as surfactants and biocides, and can be used as hydraulic fluids when of sufficiently low molecular weight, and as chemical intermediates.

Cosurfactants function as coupling agents for surfactants and reservoir brines for the purpose of enhancing crude oil production. Surfactant and cosurfactant mixtures are dissolved in brines in low concentration to form micellar fluids or solutions. These micellar solutions can be described as microemulsions containing surfactants which act to reduce the interfacial tension between water and oil. A second component, a cosurfactant, usually an alcohol, is used to improve the quality of the micellar solution. An efficient cosurfactant increases the micelles' capacity to solubilize more oil or water and still form stabilized solutions.

Compounds used as cosurfactants in the prior art have been alcohols such as isopropyl alcohol, amyl and hexyl alcohols and their ethoxylated derivatives. These cosurfactants have limited capabilities because of the variety of reservoir conditions encountered in enhanced oil recovery programs. For example, special systems must be designed for reservoirs which are essentially fresh water, that is, those which contain 6000 ppm or less monovalent ions, and those which are essentially hard water, those which contain 50,000 ppm monovalent ions plus 500 ppm or more of divalent ions. Cosurfactants should perform so as to achieve a stable fluid when the water-cosurfactant mixture is in contact or mixed with crude oil. Molecular weight of the cosurfactant should be sufficiently low to permit passage through semipermeable rock formations and achieve mobility control.

This invention accordingly also relates to a new and unique family of low molecular weight compounds which are suitable for use as cosurfactants for enhanced crude oil recovery. These compounds in use lower the interfacial tension between water and oil, are low molecular weight of from about 400 to about 1200, and are required in only low concentrations to formulate micellar fluids.

BACKGROUND OF THE INVENTION

Tricyclo(4.2.2.0$^{2,5}$)dec-9-ene-3,4,7,8-tetracarboxylic dianhydride, a known compound, is the adduct of two moles of maleic anhydride and one mole of benzene. It has the structure:

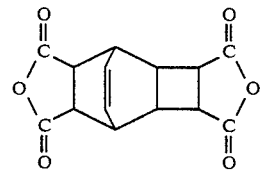

It is known to react maleic anhydride with benzophenone in benzene solution by exposing the reaction mixture to direct sunlight to prepare tricyclo(4.2.2.0$^{2,5}$)dec-9-ene-3,4,7,8-tetracarboxylic-3,4,7,8-dianhydride (D. Bryce-Smith, et al., *Chem & Ind.* (London) 1962, 2060). D. Bryce-Smith, et al., obtained 93% yield by exposing 14 g of maleic anhydride and 2.8 g of benzophenone in 265 ml of benzene in a Pyrex tube to direct sunlight for 72 hours. The tetraallyl esters of these compounds are reacted with a mercaptan and oxygen in the presence of a dye sensitizer under irradiation by visible light. The products, the title compounds, are tetraesters in which the ester moieties have been converted from —O—CH$_2$CH=CH$_2$ to —O—CH$_2$—CH(OH)—CH$_2$—SO—R, i.e., beta-hydroxysulfoxide derivatives of the original allyl esters of tricyclo(4.2.2.0$^{2,5}$)dec-9-ene-3,4,7,8-tetracarboxylic acid.

Beta-hydroxyalkylsulfoxides can be prepared by the method of Anderson, U.S. Pat. No. 3,247,258, which is incorporated by reference, wherein the mercaptan (or thiol), the olefin and oxygen are in contact at temperatures above 80° C. Anderson indicates that with certain olefins and mercaptans such as indene, styrene and thiophenol, the reaction occurs by mixing the olefin and mercaptan first, with the oxygen being bubbled through the mixture thereafter. Other patents such as Oswald, et al., U.S. Pat. No. 3,043,824 and Goodhue, et al., U.S. Pat. No. 3,210,243, which are each incorporated by reference, disclose preparing beta-hydroxyalkylsulfoxides through (1) a co-oxidation route using a hydroperoxide or through (2) oxidation of the sulfide by means of hydrogen peroxide. Oswald indicates that the preparation of hydroperoxide products by olefin-mercaptan co-oxidation to the sulfoxide requires chain initiators, e.g., ultraviolet light and the addition of peroxide compounds (hydroperoxides). In the absence of such catalysts, some co-oxidation reactions have extremely long induction periods and are not practical to carry out. Goodhue teaches that preparation of the sulfoxide using hydrogen peroxide is a three-step synthesis through the sulfide which in turn is prepared from the mercaptan with epichlorohydrin. Fields, in commonly-assigned U.S. Pat. No. 4,040,921, incorporated herein by reference, teaches a one-step process for beta-hydroxyalkylsulfoxides by reacting an olefin and a thiol with oxygen in the presence of a dye sensitizer using visible light at a temperature from −10° C. to 70° C.

The object of this invention accordingly is to produce as new compounds the 3-sulfoxy-1,2-propylene glycols-1-esters of tricyclo(4.2.2.0$^{2,5}$)dec-9-ene-3,4,7,8-tetracarboxylic acid. These compounds are useful as cosurfactants in enhanced oil recovery, as surfactants and biocides, and as hydraulic fluids when of sufficiently low molecular weight.

SUMMARY OF THE INVENTION

The invention relates to 3-sulfoxy-1,2-propylene glycols-1-esters of tricyclo(4.2.2.0$^{2,5}$)dec-9-ene-3,4,7,8-tetracarboxylic acid which are useful as cosurfactants in enhanced oil recovery, surfactants and biocides, and as hydraulic fluids when of sufficiently low molecular weight.

DETAILS OF THE INVENTION

3-Sulfoxy-1,2-propylene glycols-1esters of tricyclo(4.2.2.0$^{2,5}$)dec-9-ene-3,4,7,8-tetracarboxylic acid are prepared by reacting the tetraallyl ester of tricyclo(4.2.2.0$^{2,5}$)dec-9-ene-3,4,7,8-tetracarboxylic acid with a mercaptan RSH, oxygen at 2–50 psig, and visible light in the presence of a dye sensitizer such as Rose Bengal or methylene blue at 0°–40° C. for 0.1 to 148 hours. The mole ratio of RSH to the tetracarboxylic ester can be 1 to 5, preferably 4. The 3-sulfoxy-1,2-propylene glycols-1-esters are prepared from an olefinic alcohol wherein the olefinic moiety has from 3 to 18 carbon atoms. Examples of olefinic alcohols useful in preparation of 3-sulfoxy-1,2-propylene glycols-1-esters are allyl alcohol and crotyl alcohol.

The thiol (or mercaptan) can be aliphatic, aromatic, alicyclic and heterocyclic and can be described as being of the general formula RSH. R preferably is a radical of from 1 to 24 carbon atoms, from methyl to tetracosyl radicals, more preferably 1 to 18 carbon atoms. Examples of R in RSH that can be used are methyl, ethyl, butyl, hexyl, octyl, hexadecyl, cyclopentyl, cyclohexyl, phenyl, naphthyl, p-tolyl, benzyl, 2-benzothiazyl, and 4-pyridyl. Examples of such thiols are methylthiol, ethylthiol, n- and isopropylthiol, n-, sec- and tert-butylthiol, n-hexylthiol, n-octylthiol, tert-octylthiol, n-dodecylthiol, n- and tert-hexadecylthiol, cyclohexylthiol, tetracosylthiol, thiophenol, thiocresol, 4-n-dodecylthiocresol, 4-tert-nonylthiocresol, pyridine-2-thiol, pyridine-4-thiol, thiophene-3-thiol, furan-2-thiol, quinoline-2-thiol, quinoline-4-thiol, phenanthridine-1-thiol, 1,3,5,triazine-2-thiol.

Preferably the thiol comprises a thiol containing 1 to 18 carbon atoms. These are preferred because they are cheap, reactive, and extend the range of derivatives to cover those soluble in various inorganic and organic solvents. One or more hydrogens of the aliphatic, alicyclic and aromatic moieties such as methyl, ethyl, isobutyl, tolyl and phenyl moieties of the above-described thiol compounds can be replaced with nonreactive radical groups such as halogens and nitro radicals and, on the alicyclic and aromatic moieties, by alkyl moieties.

The molar ratios of the reactants to prepare the 3-sulfoxy-1,2-propylene glycols-1-esters, i.e., the thiols, olefinic compound, oxygen, that can be used, can vary considerably. The thiol-olefin ratio is between 0.001 to 5 moles of thiol per mole of olefin. Substantially equimolar amounts of olefin and thiol are preferred. Use of a solvent such as heptane, hexane, benzene, acetone, or dioxane at concentrations of 1 to 85 weight percent is convenient. When water-miscible solvents such as acetone or dioxane are used, water up to 50% by weight of organic solvent may be incorporated. In such cases, or when water is used with immiscible solvents such as heptane or benzene up to 50% by weight, phase-transfer agents such as cetyl trimethyl ammonium bromide, benzyl triethyl ammonium chloride, benzyl triphenyl phosphonium chloride, etc., are incorporated at concentrations of 0.001 to 1% by weight of total solvent.

Heptane is the preferred solvent.

It is essential that at least one optically sensitizing dye be used in conjunction with the application of visible light. The term dye sensitizer can be defined as being an organic dye which increases spectral response. Typical dye sensitizers are fluorescein derivatives, methylene blue, certain porphyrins and polycyclic aromatic hydrocarbons. Suitable dye sensitizers include Rose Bengal, methylene blue and Eosin.

Rose Bengal and methylene blue are the preferred dye sensitizers dissolved in acetone at 0.1–5% by weight. Sufficient dye is added to give final concentrations of 0.02 to 1% by weight in the total reaction mixture; 0.05 to 0.25% by weight is preferred. Alternatively the dye may be introduced bound to an ion-exchange resin in a relatively insoluble form, e.g., anionic Rose Bengal or Eosin attached to the strongly basic anion exchange resin Amberlite IRA-400 (Rohm and Haas, Philadelphia) or cationic methylene blue attached to the strongly acidic cation exchange resin Amberlite IRC-200 (J. R. Williams et al., *Tetrahedron Letters*, 4603 (1973)).

The reaction may be run in any type of open or sealed vessel, suitably agitated. A particularly useful apparatus for the reaction is the Parr Pressure Reaction Apparatus, Item No. 3911, made by the Parr Instrument Company of Moline, Ill. This apparatus consists of a heavy-walled clear Pyrex bottle connected with a tank of oxygen under pressure; the bottle is shaken vigorously during the reaction. Pressures of oxygen of 1 to 250 psig may be used; 15 to 50 psig $O_2$ are convenient pressures in the laboratory although, commercially, pressures over 100 psig are preferred. The bottle is illuminated with visible light such as ordinary incandescent or photoflood bulbs of 50–500 watts, preferably mounted in reflector with the light source $1\frac{1}{2}$ to 3 inches from the vessel.

The lamps used were General Electric 500 watt photoflood or incandescent bulbs and a General Electric 275 watt sunlamp. Specifications of the G.E. 500 watt photoflood lamp require 1.61 radiated watts from 280 to 400 nanometers, and 6.9 radiated watts from 400 to 700 nanometers, the range of visible light. The G.E. sunlamp has 4.47 radiated watts in the ultraviolet range from 280 to 400 nanometers, and 7.03 radiated watts in the visible light range of 400 to 700 nanometers.

Reaction is continued until the calculated amount of oxygen has been absorbed as shown by pressure drop; times of 1 to 100 hours may be used, depending on the nature of the olefin, the thiol, and the pressure of oxygen. Workup generally consists of evaporating the reaction mixture at 30°–60° C. and 0.1–1 torr, conveniently in a rotating RINCO evaporator (BUCHI Vacuum Rotary Evaporator ROTAVAPOR EL, Rinco Instrument Company, Inc., Greenville, Ill.).

The present invention also comprises a method of injecting a micellar slug into a subterranean formation comprising the steps of (1) contacting said subterranean formation with an aqueous fluid composition comprising water, a surfactant, a hydrocarbon, an electrolyte, and a low molecular weight cosurfactant within the range of from about 400 to about 1200 of a sulfoxy propylene glycol ester; (2) applying sufficient pressure to said composition to cause said micellar slug to move through said formation; (3) maintaining sufficient pressure while injecting said composition into said formation. The said low molecular weight sulfoxy propylene glycol esters can be selected from the group consisting of compounds prepared from thiophenol, methyl mercaptan, ethyl mercaptan, and n-octyl mercaptan.

In order to facilitate a clear understanding of the invention, the process of preparing 3-sulfoxy-1,2-propylene glycols-1-esters of tricyclo(4.2.2.0$^{2,5}$)dec-9-ene-3,4,7,8-tetracarboxylic acid and the use thereof, the following specific embodiments are described in detail. It should be understood, however, that the detailed expositions of the instant invention, while indicating preferred embodiments, are given by way of illustration only since various changes and modifications within the spirit and scope of the invention will become apparent to those skilled in the art from this detailed description.

PRELIMINARY EXAMPLE

Screening tests for suitable cosurfactants to be used as additives for enhanced oil recovery have been developed which indicate a relationship exists between interfacial tension of the cosurfactant and petroleum removal from core samples using a micellar solution. Surfactant-stabilized dispersions of water in hydrocarbon are micellar solutions. In addition to the required surfactant, water and hydrocarbon micellar solutions can contain cosurfactants and electrolytes to improve stability. Alcohols such as isopropanol and amyl alcohols typically have served as cosurfactants. Sodium chloride and sodium sulfate are examples of electrolytes that are used.

Important aspects of a micellar solution include an ability to solubilize water, compatibility with hydrocarbon and crude oil, an increasing viscosity with increased water concentration and inversion to an oil-in-water solution. In a micelle, surfactant and cosurfactant surround dispersed water which exists in the hydrocarbon phase as spherical droplets. With additional water, the water droplets increase in size. When water is the dispersed phase, the micellar solutions exhibit hydrocarbon-like properties of the external phase. As more and more water is solubilized in a micellar system, spheres enlarge until inversion takes place to form an oil-in-water emulsion. Cosurfactants in a micellar solution stabilize the solution to reduce incidence of inversion and phase separation.

The following bench test has been devised as a preliminary vial screening test to eliminate need for expensive core tests of cosurfactants. The test has been found to have reliability in predicting suitable properties of cosurfactants when used in micellar solutions. The principal important aspect has been found to be the interfacial tension of the cosurfactant in an oil-water mixture. The formulation is required to yield stable fluids in brine and to show low interfacial tension (IFT) as well as very good miscibility with crude petroleum.

Micellar fluids formulated from concentrates containing 40:1 to 5:1 surfactant-cosurfactant ratios have been tested over a wide range of salinities (sodium chloride in water) and hard waters, being examined for phase stability, fluid clarity, interphase behavior and miscibility of aqueous fluids with crude petroleum.

The vial screening bench test is an empirical test which comprises mixing the micellar fluid and crude petroleum by swirling the fluids together in a test tube while observing the interface. A light source is used to observe the fluid-oil behavior. The interfacial mixing (and hence interfacial tension) is judged upon a scale of very low, moderately low, low, medium and high by a comparison with standards previously developed.

For example, brine solutions of a hardness range from under 6,000 ppm of monovalent ions (sodium chloride) to about 50,000 ppm of monovalent ions (sodium chloride) are mixed with a 40:1 ratio of surfactant-cosurfactant mixture with Second Wall Creek crude. The surfactant is a petroleum sulfonate. Surfactant-cosurfactant-brine mixtures are prepared at ambient temperature and pressure.

Stability of the brine solution with surfactant-cosurfactant mixture is tested by pouring the mixture into a 50 ml graduated cylinder and allowing the solution to stand for one hour undisturbed. Fluids which remained single phase and free of sediment are further tested. 20 ml of solution are poured into a vial. 4 ml of crude petroleum are added to the vial. The vial is turned gently, observing mixing behavior of crude and micellar fluid. The vial is then shaken vigorously for one minute, after which the vial is allowed to stand undisturbed for one hour. After this period, the fluid is evaluated for oil drop-out, number of liquid phases, thickness of emulsion and miscibility. Results are correlated with interfacial tension of solution and crude by visual observation and spinning drop method of J. L. Caylas, et al., "Low Interfacial Tension," American Chemical Society Series No. 8 *Adsorption At Interfaces,* 1975. Formation of round oil droplets which separate quickly and failure to form an emulsion indicate a high, ineffective interfacial tension characteristic which can render the cosurfactant unsuitable as an additive for enhanced oil recovery applications.

EXAMPLE I

Tricyclo(4.2.2.0$^{2,5}$)dec-9-ene-3,4,7,8-tetracarboxylic-3,4,7,8-dianhydride was prepared by a modification of the method of D. Bryce-Smith, A. Gilbert, and B. Vickery, *Chemistry and Industry* (London) 1962, 2060. They obtained a 93% yield by exposing a solution of 14 g of maleic anhydride and 2.8 g of benzophenone in 265 ml of benzene in a stoppered Pyrex tube to direct sunlight for 78 hours. I refluxed a solution of 29.4 g (0.3 mole) of maleic anhydride and 3.56 g (0.02 mole) of benzophenone in 800 ml of benzene in a Pyrex 2 liter Erlenmeyer flask by irradiating at the bottom of the flask with a G.E. sunlamp for 16 hours. The dianhydride was filtered; 39 g, 95 mole %.

EXAMPLE II

A mixture of 18.7 g (0.068 mole) of the dianhydride of Example I, 40 ml of allyl alcohol, 30 ml of toluene, and 1 g of p-toluenesulfonic acid was refluxed for 18 hours with a Stark-Dean water trap. Water, 3 ml, was collected in the trap. The cooled mixture was washed with 2N NaOH, twice with water, dried over anhydrous sodium sulfate, filtered, and distilled to a pot temperature of 125° C. at 200 torr. The residue crystallized slowly. It was slurried with ether:hexane 1:1, chilled at −60° C., and filtered, giving 22.7 g white crystals of tetraallyl tricyclo(4.2.2.0$^{2,5}$)dec-9-ene-3,4,7,8 tetracarboxylate mp. 68°-69° C. Analysis: Calcd. for $C_{26}H_{30}O_8$: C,66.4; H,6.4. Found: C,66.4; H,6.7.

EXAMPLE III

A mixture of 19.9 g (42.68 mmoles) of the tetraallyl ester of Example II, 24.67 g (169 mmoles) of n-octyl mercaptan, 100 ml of benzene, and 10 ml of 0.25% Rose Bengal in acetone was shaken in a Parr Instrument shaker at 25° C. under 25 psig $O_2$ and irradiation with a G.E. sunlamp. Over 96 hours 7 lb. $O_2$ were absorbed. The solution was filtered and evaporated in a Rinco evaporator at 40° C. and 0.2 torr to give the product I where R=n-$C_8H_{17}$, 43.86 g, 95 mole %, as a light-brown, viscous oil. Analysis: Calcd. for $C_{58}H_{102}S_4O_{16}$: C,58.9;H,8.6;S, 10.8. Found: C,59.7; H,8.9; S,11.2.

EXAMPLE IV

Interfacial tension of the compound of Example III was determined at 1 (wt)% concentration between solvent-extracted 5W oil and double-distilled water. The control contained no compound of Example III. A Cenco-Du Nouy Interfacial Tensiometer No. 70545 with a 6 cm platinum-iridium ring at 25° C. was used with these results:

| Product of Example No. | Interfacial Tension, dynes/cm |
|---|---|
| Control | 41.73 |
| III | 3.87 |

EXAMPLE V

The compound of Example III was tested in the vial test as cosurfactant for enhanced oil recovery, using 5% pretroleum sulfonate as surfactant in 0.8N brine (NaCl), adding the cosurfactant to surfactant at a ratio of 1:20, and noting the stability of the mixture, as brine tends to cause the surfactant to separate (salt) out. The brine-surfactant-cosurfactant mixture, 20 ml, was then mixed by shaking with 2.5 ml of crude petroleum and the interfacial tension (IFT) observed. Low IFT was indicated by easy mixing of the two phases with no separation. Formation of round oil droplets that separate quickly indicates a high, ineffective IFT.

Product of Example III proved effective in lowering the IFT in the vial test, giving mixtures of brine-surfactant-cosurfactant fluids which were stable, did not separate, and easily formed mixtures of the fluid with crude petroleum.

EXAMPLE VI

Control of microorganisms in inhibiting or preventing growth of fungi in enhanced oil recovery operations is a desirable characteristic of useful additives.

The product of this invention was tested as a biocide and inhibitor for the growth of microorganisms by this test: 25 g of agar preparation were placed in standard petri dishes. The agar preparation consisted of 23.5 g of Bacto Plate Count Agar, Difco Laboratories, Detroit, Mich., dissolved in 1 liter of water. Plate Count Agar contains a standard USP formula for nutrient agar, consisting of:

| | |
|---|---|
| 5 g | Pancreatic digest of casein |
| 2.5 g | Yeast extract |
| 1 g | Glucose |
| 15 g | Agar |

Four petri dishes were untreated and used as blanks. To the others, in duplicate, were added 2.5 ml of 1% acetone solutions of the product of Example III. All plates were uncovered for 4 hours to expose them to the spores of adventitious fungi and bacteria, then covered and stored at 30° C. for 6 days. Ratings were given at this point; 0 represents no growth, 5 shows luxuriant colonies of fungi and bacteria. Results were as follows:

| Product of Example No. | Growth |
|---|---|
| Control | 5,5 |
| III | 0,0 |

EXAMPLE VII

A micellar slug for micellar flooding consisting of 3 (vol)% petroleum sulfonate as surfactant, 2 (vol)% petroleum hydrocarbon, 1 (vol)% cosurfactant comprising a 3-sulfoxy-1,2-propylene glycol-1-ester, prepared from the allyl esters of tricyclo (4.2.2.0$^{2,5}$) dec-9-ene-3,4,7,8-tetracarboxylic acid and n-octyl mercaptan, in a 1.0N NaCl brine solution is prepared. The micellar slug fluid is fed into the high pressure injection pump and is injected into a 25 foot section sandstone formation in Crawford County, Illinois, USA, through an injection well at 900 psig. The amount of slug injected is about 7% of reservoir pore volume, and the petroleum hydrocarbon is lease crude oil. Pattern of injection is two rows of injection wells and three rows of producer wells. There are nine wells in each row and total area enclosed is 40 acres. Injection and production wells are 460 feet apart and adjacent wells are 115 feet apart. Crude oil production increases to recover about 30% of the oil in place at start of the injection.

What is claimed is:

1. A method of injecting a micellar slug into a subterranean formation comprising the steps of:
   (1) contacting said formation with an aqueous fluid composition comprising water, a surfactant, a hydrocarbon, an electrolyte and a cosurfactant comprising 3-sulfoxy-1,2-propylene glycols-1-esters of tricyclo (4.2.2.0$^{2,5}$) dec-9-ene-3,4,7,8-tetracarboxylic acid of molecular weight of from about 400 to about 1200,
   (2) applying sufficient pressure to said composition to cause said micellar slug to move through said formation,
   (3) maintaining sufficient pressure while injecting said composition into said formation.

* * * * *